United States Patent [19]

McGuire

[11] Patent Number: 4,681,850

[45] Date of Patent: Jul. 21, 1987

[54] PHENYLALANINE AMMONIA LYASE-PRODUCING MICROBIAL CELLS

[75] Inventor: Jeffrey C. McGuire, Frederick, Md.

[73] Assignee: Genex Corporation, Gaithersburg, Md.

[21] Appl. No.: 673,332

[22] Filed: Nov. 20, 1984

[51] Int. Cl.$^4$ .................... C12N 1/14; C12N 15/00; C12P 13/22; C12R 1/645

[52] U.S. Cl. .................... 435/254; 435/108; 435/172.1; 435/911

[58] Field of Search ............... 435/108, 232, 174, 911, 435/178, 172.1, 175, 176, 177, 254

[56] References Cited

U.S. PATENT DOCUMENTS 3,654,079  4/1972  Tanaka et al.
3,660,235  5/1972  Okumura et al.
3,909,353  9/1975  Tsuchida et al.

FOREIGN PATENT DOCUMENTS 1489468  10/1977  United Kingdom .

OTHER PUBLICATIONS

Yamada et al, "Production of L-Phenylalanine from Trans Cinnamic Acid with Rhodotorula Glutinis Containing PAL Activity", Applied and Environmental Microbiology 42(5), pp. 773–778, (1981).

Gilbert et al, "Synthesis and Degradation of Phenylalanina Ammonia-Lyase of Rhodosporidium Toruloides", Journal of Bacteriology 150(2), pp. 498–505, (1982).

Miller et al, "The Operon", Cold Spring Harbor Lab, 1980, pp. 31–56.

Müller-Hill et al., Biochemistry, vol. 59, pp. 1259–1264, 1968.

Kodansha et al., The Microbial Production of Amino Acids, pp. 40–66, 1972.

LaManna and Mallette, Basic Bacteriology, 2nd Ed., pp. 626–649, 1959.

Nakamichi et al., Applied and Environmental Microbiology, vol. 42, No. 6, pp. 773–778, Nov. 1981.

Primary Examiner—Charles F. Warren
Assistant Examiner—John E. Tarcza
Attorney, Agent, or Firm—Saidman, Sterne, Kessler & Goldstein

[57] ABSTRACT

This invention relates to novel microbial strains which produce phenylalanine ammonia-lyase in the absence of an inducer. Also disclosed is a method for making phenylalanine.

1 Claim, No Drawings

PHENYLALANINE AMMONIA LYASE-PRODUCING MICROBIAL CELLS

BACKGROUND OF THE INVENTION

The present invention relates to novel phenylalanine ammonia-lyase-producing microorganisms and a method for their selection and use. More particularly, the invention concerns microorganisms which produce relatively high levels of the enzyme, phenylalanine ammonia-lyase (hereinafter referred to as PAL) in the absence of known inducers. PAL, in turn, is useful for the production of L-phenylalanine.

L-phenylalanine is an essential amino acid in man and is, therefore, an important ingredient of enteral and parenteral nutritional formulations. In addition, this amino acid is useful as a starting material for the production of other products, such as the artificial sweetener, aspartame. Various microbial processes for the production of phenylalanine are known. For example, U.S. Pat. No. 3,660,235 describes the production of phenylalanine by phenylalanine analog resistant strains of Brevibacterium, Corynebacterium, Arthrobacter, Bacillus, and Candida. The production of this amino acid by tyrosine-requiring mutants of certain strains of Brevibacterium, Corynebacterium, Arthrobacter, and Escherichia is also known. See U.S. Pat. Nos. 3,654,079 and 3,909,353.

PAL catalyzes the breakdown of L-phenylalanine to trans-cinnamic acid and ammonia. This enzymatic reaction is reversible, and British Patent No. 1,489,468 discloses a process for the production of L-phenylalanine which involves the PAL-catalyzed reaction of trans-cinnamic acid with ammonium ions to yield L-phenylalanine. This reaction is useful for producing L-phenylalanine and, therefore, there is a continuing need to obtain production microorganisms which produce high levels of PAL activity. Such microorganisms can be used directly for the conversion of cinnamic acid and ammonium ions to L-phenylalanine, or the enzyme can be isolated from the cells and used to produce L-phenylalanine in various forms of bioreactors.

Microbial biosynthesis of PAL is highly regulated and current production strains require the use of an inducer to elicit PAL synthesis. This inducer, usually L-phenylalanine, contributes to the total raw material costs of PAL fermentation. Therefore, the commercial need for a microorganism that can synthesize PAL in the absence of an inducer persists.

SUMMARY OF THE INVENTION

In accordance with the present invention, PAL-constitutive mutants are disclosed and are selected by growing mutants of PAL-producing microorganisms on a non-inducing nutritional medium, incubating to allow colony formation, and immunologically screening the colonies for PAL. This invention provides a mutant that produces PAL in the absence of conventional inducers. The screen can be used to select PAL-constitutive mutants of any PAL-producing microorganisms, and is particularly useful in obtaining yeast mutants of the genera Rhodotorula and Rhodosporidium. These cells can be used directly for the conversion of cinnamic acid and ammonium ions to L-phenylalanine, or the enzyme can be isolated from the cells and utilized in the production of L-phenylalanine.

DETAILED DESCRIPTION OF THE INVENTION

The microbial strains of the present invention are obtained by conventional mutation procedures. Such procedures include, for example, exposing a culture of a parent strain to chemical mutation, using a mutagen such as nitrosoguanidine, ethylmethane sulfonate, 5-bromouracil, hydroxylamine, nitrogen and sulfur mustards, and the like. Irradiating the cells with ultraviolet light or ionizing radiation can also be employed. Such techniques are well known, and are described, for example, in *Basic Bacteriology*, LaManna and Mallette, Second Edition, the Williams & Williams Company, Baltimore, Md., 1959, on pages 646 to 649.

Chemical or radiation induced mutation typically produces hundreds to thousands of mutant strains. Selecting viable strains that have the desired characteristics is an arduous task, unless a specific selection procedure can be devised. The present invention involves a selection procedure for PAL constitutive mutants whereby the mutants are grown on a non-inducing nutrient medium and colonies are then immunologically screened for PAL. In many wild-type and production yeast strains, the biosynthesis of PAL is repressed by carbon catabolites. Hence, the selection medium is preferably free of glucose or other catabolite-repressing nutrients. The microorganisms of the present invention make PAL in the absence of phenylalanine, but may still be subject to catabolite repression.

Microbial cells that can be obtained by these procedures include bacteria of the genus Streptomyces and yeasts of the genera Rhodotorula, Rhodosporidium, and Sporobolomyces. After producing mutants from wild type or known PAL-producing strains, the mutant population is transferred to a minimal essential medium, for example, by means of replica plating on sterile nitrocellulose filters.

Minimal essential media are well known, and typically include phosphate, sulfate, chloride, iodide, and molybdate salts of potassium, sodium, iron, manganese, and zinc in concentrations of from 0.05 to about 1.0 gram per liter. In addition, these media advantageously contain vitamins and growth factors such as biotin, calcium pantothenate, folic acid, inositol, niacin, p-aminobenzoic acid, pyridoxine hydrochloride, riboflavin, and thiamine hydrochloride, in amounts ranging from about 0.1 to about 1.0 gram per liter. The composition of the medium is not critical, and may be composed of a variety of synthetic, semi-synthetic, or natural ingredients.

The minimal essential medium preferably contains a carbon source that is not catabolite repressing. Examples of such carbon sources include galactose and maltose. The medium is substantially devoid of L-phenylalanine or other PAL inducers.

The selection media are preferably solid media (e.g., agar media) to facilitate handling and transfer of cells. These media are sterile and are buffered to a physiologically acceptable pH, e.g., from about 5 to about 8, preferably from about 6 to about 7. Inoculated media are incubated at biologically acceptable temperatures e.g., from about 20° C. to about 50° C., preferably about 30° C.

The selection procedure of this invention includes an immunological screen of putative PAL-constitutive colonies. The first step of the screening procedure (growth on a non-inducing medium) typically produces thousands of potential PAL-constitutive mutants. To analyze cultures of these mutants for PAL by conventional procedures would be impractical. Accordingly, a quick and reliable immunological screen has been devised which employs an anti-PAL antibody. The anti-PAL antibody is produced by immunizing mice with commercially available PAL and recovering the antiserum by conventional means. The immunological screen may be accomplished using a variety of types of equipment and reaction techniques. For example, identification of PAL-producing colonies may be accomplished using enzymeimmunoassay, radioimmunoasay or other such techniques.

A convenient procedure involves transferring mutant colonies from non-inducing media to a solid surface, such as a nitrocellulose filter. The cells are then lysed, e.g., by freezing with liquid nitrogen, and the nitrocellulose filter is contacted with the antiserum. After sufficient incubation, unbound anti-PAL antibody is washed from the surface and positive reactions are identified by contacting the surface with a second antibody (e.g., goat anti-mouse IgG) which has been labelled for visualization or detection by other means. These procedures are effective for identifying PAL-producing colonies and reducing the total number of potential PAL-constitutive mutants to a manageable number.

Microbial colonies which are selected by the above procedures can be further analyzed quantitatively for PAL by culturing the mutants in media in the presence and absence of PAL-inducers such as L-phenylalanine. PAL activity of the cells is measured by standard procedures, and the specific activities of the strains can serve as an indicator of the PAL-constitutive nature of the strain.

The PAL-constitutive producing strains of this invention may be used to produce PAL by fermentation, and the PAL can in turn be utilized to enzymatically convert t-cinnamic acid and ammonia into L-phenylalanine. Generally, PAL is produced by cultivating a PAL-producing strain in a nutritional medium containing assimilable sources of carbon, nitrogen, and essential vitamins, minerals and other growth factors. Suitable carbon sources can include various refined or crude carbohydrates such as glucose, sucrose, molasses, starches, grains, and the like. A preferred carbon source is glucose syrup. Nitrogen sources include inorganic ammonium salts, such as ammonium phosphates, ammonium sulfate, ammonium acetate, ammonium citrate, ammonium nitrate, and the like, and organic nitrogenous substances such as soybean meal, meat infusion, amino acids, corn steep liquor, protein hydrolyzates, peptones, yeast extracts, and the like. A preferred nitrogen source for the process of this invention is yeast extract.

Vitamins, minerals, and other growth factors may be supplied by the carbon and nitrogen sources, or may be provided separately. These components can vary with the particular microorganism employed. Typically, trace minerals such as zinc, manganese, iron, cobalt, and calcium can be supplied in growth-promoting amounts as inorganic salts. These minerals may, for example, be supplied with process water, e.g., tap water, sea water, etc. Another growth factor typically supplied is DL-methionine. Nutrient media of the type described are well known, and can widely vary in composition.

The microorganisms disclosed by this invention are capable of producing PAL in the absence of phenylalanine or other PAL-inducer. Therefore, PAL inducer need not be added to the medium.

If the cells employed are sensitive to catabolite repression of PAL synthesis, then means should be employed to reduce or eliminate catabolites and their precursors from the medium. This may be accomplished by separating the cells from the medium, washing the cells, and suspending the cells in a catabolite-free medium. Alternatively, the cells can be allowed to grow until the nutrients are substantially exhausted before recovering PAL.

PAL produced by these procedures may be employed to produce L-phenylalanine from t-cinnamic acid and ammonia. These reactants can be added directly to the PAL-containing cells or enzyme isolated therefrom can be immobilized by known procedures on a solid support that can be reused for so long as the enzyme activity is maintained.

Phenylalanine is produced by this method under phenylalanine-producing conditions. These conditions will vary, depending upon the particular microbial strains employed, whether whole cells or cell-free enzyme preparations are used and whether immobilized systems are employed. In general, t-cinnamic acid and aqueous ammonia (or soluble ammonium salts) are supplied in amounts such that aqueous ammonia or ammonium salts are in excess. Aqueous ammonia and ammonium salts are employed in amounts from about 3 to about 8 moles per liter. The purpose of the high ammonia concentration is to obtain a high rate of conversion of t-cinnamic acid into phenylalanine. The t-cinnamic acid is employed in amounts of from about 5 to about 30 grams per liter. The concentration of t-cinnamic acid in the reactor is maintained within these ranges by periodic additions of t-cinnamic acid. The pH is maintained within the range of 9.5–11, preferably 10.4–10.8. The temperature is generally maintained within the range of 15°–35° C.

L-phenylalanine produced by these methods can be recovered by any suitable means. The solubility of this amino acid is relatively low; therefore, often the product will precipitate from the reaction mixture when the pH is adjusted to its isoeletric point (5.5), and can be recovered by filtration or centrifugation. The product can then be further purified, if desired, by recrystallization or column chromatography.

The following examples will serve to illustrate this invention without limiting the invention thereto:

GENERAL PROCEDURE

Strains. *Rhodotorula rubra* strain GX3243, NRRL-Y-15597, the starting strain for the experiments described below, was maintained on YPD agar (see below). Growth in liquid culture was followed by monitoring optical density at 560 nm. An optical density of 1.0 corresponds to approximately 0.37 g/l dry weight. All cultures were incubated at 30° C.

Media. YE medium contained 15 g of yeast extract per liter. YPD medium contained 20 g per liter of Bacto-peptone (Difco Laboratories, Detroit, Mich., USA), 10 grams per liter of yeast extract, and 20 grams per liter of glucose. Minimal media all contained, per liter, 1 gram potassium phosphate, 0.5 gram magnesium sulfate, 0.1 gram sodium chloride, 0.1 gram calcium chloride, and 0.4 milligram each of biotin, calcium pantothenate, folic acid, inositol, niacin, para-amino benzoic acid, pyridoxine hydrochloride, riboflavin, thiamine hydrochloride, boric acid, potassium iodide, ferric chloride, manganese sulfate, sodium molybdate, and zinc sulfate. The minimal media also contained 5 grams per liter of a carbon source and 5 grams per liter of a nitrogen source. Solid media contained 20 grams of agar per liter in addition to the above components.

Mutagenesis. Cultures grown in YPD or YE media were centrifuged and resuspended in PA medium at an optical density of 1. N-methyl-N'-nitro-N-nitrosoguanidine (NTG) was added to a final concentration of 10–15 Milligrams per liter. The cultures were incubated with shaking for 30 minutes at 30° C., and were washed before being diluted and plated. Cells subjected to ethylmethane sulfonate (EMS) mutagenesis were treated as above, except NTG was replaced by EMS to a final concentration of 5 mg/ml. After exposure to EMS for 60 minutes at 30° C., cells were washed and plated.

PAL Induction. For PAL induction, strains were inoculated from agar plates into 5 ml YPD medium and incubated at 30° C. with shaking. At optical density of 5–15 at 560 nm (48–72 hours after inoculation), the cultures were centrifuged at 6000 X g for 10 minutes. The cell pellets were resuspended in PA medium at an optical density of 1.0. The cultures were then incubated at 30° C. with shaking for 4½–7 hours. PAL activity and optical density were then measured.

PAL Assay. PAL was measured by addition of a 10–100 microliter cell sample to 1 ml of a solution composed of 50 mM Tris buffer (pH 8.8), 25 mM 1-phenylalanine, and 0.001% (w/v) of cetylpyridinium chloride. This mixture was incubated in a recording spectrophotometer and the appearance of cinnamic acid was followed at 280 nm (molar absorbance=16,200). The rate of increase in optical density was measured during a period of linear increase, usually between one and five minutes after addition of cells. A unit of PAL is the amount of enzyme catalyzing the formation of one micromole of cinnamic acid per minute at 30° C. Specific activities are expressed as units of PAL per gram of dry cell weight (u/g).

EXAMPLE 1

R. rubra cells were mutagenized with nitrosoguanidine as described above. Mutagenized cells were plated on YPD agar at a density of 150 colonies per 100 mm plate. The plates were incubated at 30° C. After three days, colonies were transferred by nitrocellulose filter onto a plate of minimal medium. The medium contained either galactose or maltose as a carbon source.

The colonies were immunologically screened for PAL after a four to eight day incubation period. The nitrocellulose filters carrying the colonies were dipped into liquid nitrogen to lyse the cells, and the colonies were removed from the filter by washing with deionized water. The filters were then incubated for one hour at room temperature in 10% fetal calf serum followed by two 15-minute washings with Tris Buffered Saline (TBS) (0.5 M NaCl, 0.02 M Tris pH 7.5). Filters were then incubated for 18 hours at room temperature in mouse anti-PAL antiserum (diluted 1:10,000 in TBS) and washed with TBS twice for 15 minutes. Horseradish peroxidase-conjugated goat antimouse IgG1 (BioRad catalog #170-6516), diluted 1:1000 in TBS, was added, and the filters were incubated for one hour followed by two TBS washings over a fifteen-minute period. The filters were finally stained with a staining solution made by addition of 3 microliters of 30% hydrogen peroxide per ml dye solution to 3 mg/ml 4-chloro-1-napthol HRP color development reagent (BioRad catalog #170-6534) followed by addition of 5 ml TBS per ml dye solution. The color development reaction was stopped by the addition of excess deionized water upon visualization of purple color (5–30 minutes). One hundred twenty-one plates were screened, and 49 candidate colonies were identified.

EXAMPLE 2

The 49 candidate colonies identified above were transferred from the original YPD plates to galactose minimal plates and were incubated for 6–11 days. Forty-one candidates grew on the galactose plates. Those 41 candidates were tested for PAL by transferring a sample of cells from each candidate colony by mean of a toothpick into 1 ml of a solution composed of 50 mM Tris buffer (pH 8.8) 25 mM 1-phenylalanine, and 0.001% (w/v) of cetylpyridinium chloride, in a 2 ml microcentrifuge tube. The tubes were incubated for 2 hours at 37° C., then centrifuged at 13,000×g for 2 minutes. The optical density of the supernatant at 280 nm was recorded. Background OD was about 0.10. One positive candidate was identified. This isolate was designated R. rubra GX5901.

EXAMPLE 3

Strain GX5901 was tested for PAL production in inducing and non-inducing media in shake flasks. A culture of GX5901 in YPD broth (OD 560=3.0) was centrifuged, suspended in water at OD 560=0.5, and grown on phenylalanine/ammonia, galactose/ammonia, and maltose/ammonia media. A YPD culture of the parent strain of R. rubra R2T (OD 560=5.7) was grown under similar conditions, except that inoculation was at OD=0.6. Cells were periodically assayed for growth (OD 560) and for PAL activity (0.1 ml of culture assayed). The results of this experiment, illustrated in Table 1, reveal that strain GX5901 had a higher PAL specific activity than the parent strain, and this differential was most pronounced in media lacking phenylalanine.

R. rubra strain GX5901 has been deposited with the ARS Culture Collection, U.S. Department of Agriculture, Peoria, Ill. with accession number NRRL-Y 15901.

TABLE 1

| Hours Incubation | O.D. 560 | | PAL, mU/ml | | PAL, mU/mg Dry Cells | |
|---|---|---|---|---|---|---|
| | R2T | GX5901 | R2T | GX5901 | R2T | GX5901 |
| Medium: Phenylalanine/Ammonia | | | | | | |
| 6.0 | 1.5 | 0.4 | 41 | 22 | 106 | 152 |
| Medium: Galactose/Ammonia | | | | | | |
| 3.0 | ND | ND | ND | 10 | ND | ND |
| 4.5 | 1.1 | 0.85 | 2 | 10 | 5 | 33 |
| 6.0 | 0.6 | 0.5 | 3 | 9 | 12 | 48 |
| Medium: Maltose/Ammonia | | | | | | |
| 2.5 | ND | ND | ND | 24 | ND | ND |
| 3.0 | ND | ND | 9 | ND | ND | ND |
| 4.0 | ND | 0.7 | ND | 20 | ND | 79 |
| 4.5 | 0.8 | ND | 5 | ND | 17 | ND |
| 6.0 | 0.4 | 0.3 | 3 | 7 | 23 | 62 |

What is claimed is:

1. A PAL-constitutive microorganism which is capable of producing PAL in the absence of PAL inducer, wherein said microorganism is a strain of Rhodotorula rubra, said strain having the identifying characteristics of Rhodotorula rubra, strain GX-5901, NRRL Y 15901.

* * * * *